US011395920B2

(12) United States Patent
Madhavan et al.

(10) Patent No.: US 11,395,920 B2
(45) Date of Patent: Jul. 26, 2022

(54) BRAIN CONNECTIVITY ATLAS FOR PERSONALIZED FUNCTIONAL NEUROSURGERY TARGETING AND BRAIN STIMULATION PROGRAMMING

(71) Applicants: General Electric Company, Schenectady, NY (US); University Health Network, Toronto (CA)

(72) Inventors: Radhika Madhavan, Bangalore (IN); Gavin Elias, Toronto (CA); Alexandre Boutet, Toronto (CA); Suresh Joel, Bangalore (IN); Andres M. Lozano, Toronto (CA)

(73) Assignees: General Electric Company, Schenectady, NY (US); University Health Network, Toronto (CA)

( * ) Notice: Subject to any disclaimer, the term of this patent is extended or adjusted under 35 U.S.C. 154(b) by 532 days.

(21) Appl. No.: 16/253,390

(22) Filed: Jan. 22, 2019

(65) Prior Publication Data

US 2020/0230413 A1 Jul. 23, 2020

(51) Int. Cl.
*A61N 1/36* (2006.01)
*G16H 10/60* (2018.01)
(Continued)

(52) U.S. Cl.
CPC ........ *A61N 1/36082* (2013.01); *A61B 5/0042* (2013.01); *A61N 1/0534* (2013.01);
(Continued)

(58) Field of Classification Search
CPC .............. A61N 1/0534; A61N 1/36082; A61B 5/0035; A61B 5/0042; G16H 10/60
See application file for complete search history.

(56) References Cited

U.S. PATENT DOCUMENTS 9,220,458 B2 12/2015 Pouratian
2011/0307030 A1 12/2011 John
(Continued)

FOREIGN PATENT DOCUMENTS

WO 2013172981 A1 11/2013
WO 2017209673 A1 12/2017
(Continued)

OTHER PUBLICATIONS

Tang et al., A Probabilistic Atlas of Human Brainstem Pathways Based on Connectome Imaging Data, NeuroImage, vol. 169, Apr. 1, 2018, Amsterdam, NL, pp. 227-239.
(Continued)

*Primary Examiner* — Joseph M Dietrich
(74) *Attorney, Agent, or Firm* — Ziolkowski Patent Solutions Group, SC

(57) ABSTRACT

A system and method for identifying a patient-specific neurosurgery target location is provided. The system receives brain imaging data for a patient that includes tracts and networks in the patient brain, accesses a quantitative connectome atlas comprising population-based, disease-specific structural and functional connectivity maps comprising a pattern of tracts and networks associated with an optimal target area (OTA) identified from a population of patients, and defines the patient-specific neurosurgery target location based on a comparison between a pattern of the tracts and networks from the brain imaging data for the patient and the pattern of tracts and networks associated with the OTA identified from the population of patients in the quantitative connectome atlas. The quantitative connectome atlas comprises a disease-specific, population-based quantitative connectome atlas that identifies an optimal target location for treatment associated with a maximal clinical improvement for each disease in the population of patients.

20 Claims, 6 Drawing Sheets

(51) Int. Cl.
*A61B 5/00* (2006.01)
*A61N 1/05* (2006.01)
*G16H 50/70* (2018.01)

(52) U.S. Cl.
CPC ............ *G16H 10/60* (2018.01); *A61B 5/0035* (2013.01); *A61N 1/0531* (2013.01); *A61N 1/36067* (2013.01); *A61N 1/36135* (2013.01); *G16H 50/70* (2018.01)

(56) References Cited

U.S. PATENT DOCUMENTS

| | | |
|---|---|---|
| 2015/0119689 A1 | 4/2015 | Pascual-Leone et al. |
| 2015/0360039 A1 | 12/2015 | Lempka et al. |
| 2018/0104500 A1 | 4/2018 | Blum et al. |

FOREIGN PATENT DOCUMENTS

| | | |
|---|---|---|
| WO | 2018023056 A1 | 2/2018 |
| WO | 2018157909 A1 | 9/2018 |
| WO | 2019094836 A1 | 5/2019 |

OTHER PUBLICATIONS

Akram et al., "Connectivity Derived Thalamic Segmentation in Deep Brain Stimulation for Tremor," NeuroImage: Clinical 2018, vol. 18, pp. 130-142.

Akram et al., "Optimal Deep Brain Stimulation Site and Target Connectivity for Chronic Cluster Headache," Neurology 2017, vol. 89, pp. 2083-2091.

Akram et al., "Subthalamic Deep Brain Stimulation Sweet Spots and Hyperdirect Cortical Connectivity in Parkinson's Disease," Neuroimage 2017, Sep. 1, vol. 158, pp. 332-345.

Butson et al., "Probabilistic Analysis of Activation Volumes Generated During Deep Brain Stimulation," Neuroimage 2011, Feb. 1, vol. 54, No. 3, pp. 2096-2104.

Cheung et al., "Defining a Therapeutic Target for Pallidal Deep Brain Stimulation for Dystonia," American Neuroliical Association, Jul. 2014, vol. 76, No. 1, pp. 22-30.

Dembek et al., "Probabilistic Mapping of Deep Brain Stimulation Effects in Essential Tremor," NeuroImage: Clinical 2017, vol. 13, pp. 164-173.

Eisenstein et al., "Functional Anatomy of Subthalamic Nucleus Stimulation in Parkinson Disease," Ann Neurol, Aug. 2014, vol. 76, No. 2, pp. 279-295.

Frankemolle et al., "Reversing Cognitive-Motor Impairments in Parkinson's Disease Patients Using a Computational Modelling Approach to Deep Brain Stimulation Programming," Brain 2010 vol. 133, pp. 746-761.

Horn et al., "Probabilistic Conversion of Neurosurgical DBS Electrode Coordinates into MNI Space," Neuroimage 2017, Apr. 15, vol. 150, pp. 395-404.

Horn et al., "Toward an Electrophysiological "Sweet Spot" for Deep Brain Stimulation in the Subthalamic Nucleus," Human Brain Mapping, 2017, vol. 38, pp. 3377-3390.

Horn et al., "Connectivity Predicts Deep Brain Stimulation Outcome in Parkinson Disease," Ann Neurol, Jul. 2017, vol. 82, No. 1, pp. 67-78.

McIntyre et al., "Customizing Deep Brain Stimulation to the Patient Using Computational Models," Conf Proc IEEE Eng Med Biol Soc. 2009, pp. 4228-4229.

Neumann et al., "A Localized Pallidal Physiomarker in Cervical Dystonia," Ann Neurol, Dec. 2017, vol. 82, pp. 912-924.

Tsolaki et al., "The Potential Value of Probabilistic Tractography-Based for MR-Guided Focused Ultrasound Thalamotomy for Essential Tremor," NeuroImage: Clinical, 2018, vol. 17, pp. 1019-1027.

BRAIN CONNECTIVITY ATLAS FOR PERSONALIZED FUNCTIONAL NEUROSURGERY TARGETING AND BRAIN STIMULATION PROGRAMMING

BACKGROUND OF THE INVENTION

Embodiments of the invention relate generally to a system and method for neurosurgery targeting, and more particularly to a system and method for personalized functional neurosurgery targeting and brain stimulation programming that is derived from a brain connectivity atlas along with functional and structural imaging and clinical/psychometric testing.

Functional neurosurgery is a neurosurgical specialty focusing on neurodegenerative diseases and other circuit-based neurological and psychiatric disorders. Functional neurosurgeons target conditions in which the physiology of the central nervous system is altered but the gross anatomy may (or may not) be normal. Such conditions cover a wide range of neurological disorders: movement disorders (e.g. Parkinson's disease, dystonia, essential tremor), psychiatric disorders (e.g. major depressive disorder, anorexia nervosa), cognitive disorders (e.g. Alzheimer's disease) as well as other less common disorders such as chronic neuropathic pain. Functional neurosurgical treatments such as deep brain stimulation (DBS), radiosurgery, radiofrequency ablation and, more recently, MR-guided focused ultrasound (MRgFUS) are intended to therapeutically modulate abnormal brain circuitry in order to improve patients' symptoms (and possibly alter the natural course of the disease).

In order to implement functional neurosurgical treatments, a specific brain area (i.e., circuit) must be targeted. However, accurate and precise targeting of structures within the brain has always been a challenge for the field of functional neurosurgery. The first challenge is that current brain targets are based on empirical experience, dating mainly before the turn of the current century. This experience grew mainly from live intra-operative and post-mortem pathological data and more recently from animal experiments. While an optimal target location is typically well within an anatomical target area, the exact location may be slightly different for each patient depending on their symptomatology and underlying anatomy comprising networks and tracts. It is only recently that the scientific community has made attempts at refining and finding the optimal brain target, based on imaging of patient cohorts.

The second challenge is that, in many cases, desired brain targets cannot be directly visualized on conventional structural Mill. Instead, their presumed location can only be inferred or estimated with reference to indirect stereotactic coordinates in relation to anatomical landmarks (e.g., anterior and posterior commissures) and intra-operative microelectrode recordings (when available). As a result of suboptimal targeting methods, clinical outcomes may also be suboptimal. For example, the degree of improvement in DBS therapy depends to a large extent on accurate placement of electrode(s) in the target area. Similarly, inaccurate targeting is also linked with adverse effects. Still further, the exact placement of electrode(s) within the general anatomical target may be slightly different for each patient depending on their symptomatology.

A third challenge exists for patients requiring neuromodulation tuning after surgery (for example, DBS). DBS electrodes deliver constant electrical pulses to modulate targeted brain circuitry. Empirically-derived programming algorithms, which optimize clinical benefits by gradually titrating the delivered energy, require time-consuming and costly visits for patients and the health care system. The titration of electricity aims at maximizing benefits and minimizing adverse effects and is usually guided by clinical feedback, which may be immediate or delayed. This is particularly important since new electrode models have more contacts and thus more possibilities of programming to test. In addition, these new electrodes are able to preferentially steer the electricity towards one side and thus stimulate beneficial structures and avoiding stimulation of adverse-effect related structure on the opposite side.

It would therefore be desirable to have a system and method that provides for accurate and precise personalized functional neurosurgery targeting and brain stimulation programming.

BRIEF DESCRIPTION OF THE INVENTION

In accordance with one aspect of the invention, a system for identifying a patient-specific neurosurgery target location is provided. The system includes a processor programmed to receive brain imaging data for a patient that includes tracts and networks in the patient brain, access a quantitative connectome atlas comprising population-based, disease-specific structural and functional connectivity maps comprising a pattern of tracts and networks associated with an optimal target area (OTA) identified from a population of patients, and define the patient-specific neurosurgery target location based on a comparison between a pattern of the tracts and networks from the brain imaging data for the patient and the pattern of tracts and networks associated with the OTA identified from the population of patients in the quantitative connectome atlas.

In accordance with another aspect of the invention, a computer-based method for deriving a disease-specific, population-based quantitative connectome atlas is provided. The method includes accessing a database comprising data on a population of patients having previously undergone functional neurosurgical treatment and on a healthy control population of patients, the data comprising structural and/or functional brain imaging data, and clinical outcomes for the population of patients, for each of a plurality of diseases. The method also includes identifying a treatment area for each patient in the population, the treatment area comprising a lesion location when the functional neurosurgical treatment is an ablative procedure or an electrode location, and corresponding volume of tissue activated (VTA) when the functional neurosurgical treatment is deep brain stimulation (DBS). The method further includes weighting the treatment area for each patient based on symptom improvement resulting from the functional neurosurgical treatment and averaging the weighted treatment areas across the population of patients to identify an optimal target area (OTA) associated with a maximal clinical improvement in each of a number of disease cohorts in the population of patients.

In accordance with yet another aspect of the invention, a computer-based method for identifying a patient-specific neurosurgery target location is provided. The method includes accessing a population-based, disease-specific brain connectivity atlas derived from a population of patients having previously undergone functional neurosurgical treatment, with data collected on each of the patients comprising brain imaging data and clinical outcomes for the patient, for each of a plurality of diseases. The method also includes identifying, from the brain connectivity atlas, one or more optimal neurosurgery target locations associated with optimal treatment of the patient.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Figure 1:
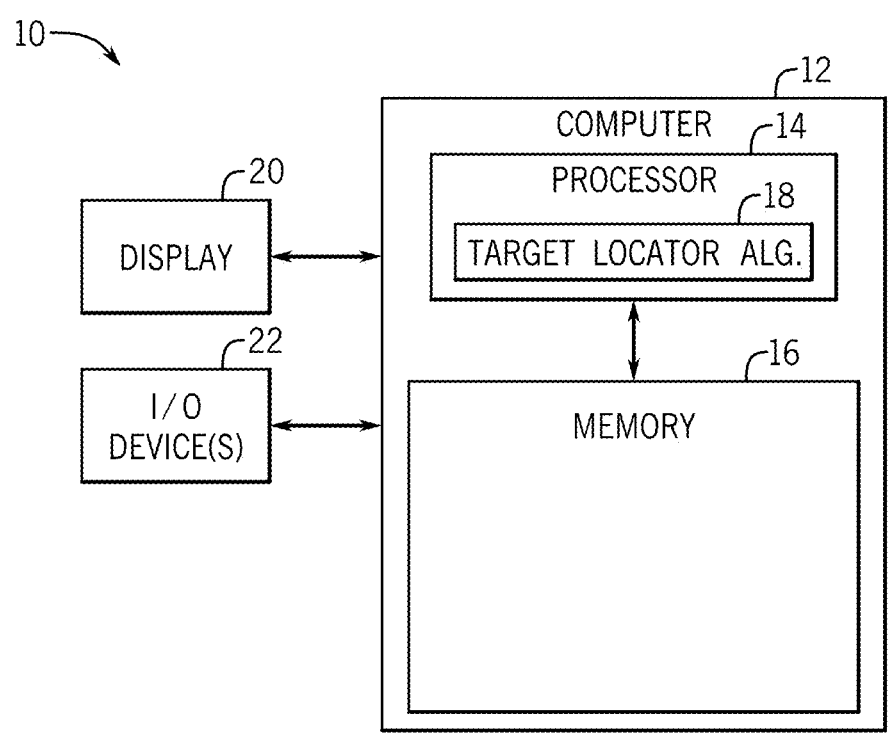
FIG. 1 is a schematic block schematic diagram of a system for identifying a patient-specific neurosurgery target location for patient treatment, according to an embodiment of the invention.

In general, embodiments of the invention described herein are directed to a system and method for personalized functional neurosurgery targeting and brain stimulation programming. Accurate neurosurgery targeting is achieved via use of a population-based brain connectivity atlas encompassing various neurological diseases, with the atlas being used in pre-surgical planning to identify a patient-specific neurosurgery target location that will provide maximal symptom relief.

As used herein, the terms "stimulation," "stimulated," "activation," and "activated" refer to any artificial input that causes one or more neuromodulatory effects (e.g., excitation/activation, inhibition, conduction block, modulation of response to other inputs, or the like) in at least a portion of neurons in a target tissue. The stimulation can be electrical stimulation and the target tissue can be neural tissue, such as a portion of the brain. Accordingly, the stimulation can be used for deep brain stimulation, according to an exemplary embodiment.

As used herein, the term "imaging" can refer to a technique of creating a visual representation of the interior of a body for clinical analysis. Examples of medical imaging can include structural imaging and functional imaging. Structural imaging can reveal the underlying structure of at least a portion of the body. Functional imaging can provide direct or indirect measurements of physiological activity (e.g., neural activity). Examples of functional imaging modalities can include functional magnetic resonance imaging (fMRI), diffusion-weighted imaging (DWI), evoked potentials, local field potential (LFP), electrocorticography (ECoG), electroencephalography (EEG), magnetoencephalography (MEG), electromyography (EMG), positron emission tomography (PET), magnetic resonance spectroscopy (MRS), single-photon emission computed tomography (SPECT), near-infrared (NIR) spectroscopy, optical tomography (OT), ultrasound, laser Doppler measurements, and the like.

As used herein, the terms "optimal" and "sub-optimal" can be measures of clinical efficacy. For example, when a target location or stimulation is deemed optimal, it can refer to a target location or stimulation parameter being used that produces a clinically relevant outcome. When a target location or stimulation is deemed sub-optimal, it can refer to a target location or stimulation parameter being used that produces an outcome above/below clinical relevance. For example, in some instances, a sub-optimal target location or stimulation is 10% or more different than a clinically relevant target location or stimulation. In some instances, a sub-optimal target location or stimulation is 5% or more different than a clinically relevant target location or stimulation.

As used herein, the term "functional neurosurgical treatment" may refer to a neurosurgical treatment used to treat neurodegenerative diseases and other circuit-based neurological and psychiatric disorders. Functional neurosurgical treatments can thus include treatments such as DBS, radiosurgery, radiofrequency ablation and MRgFUS that therapeutically modulate abnormal brain circuitry in order to improve patients' symptoms and potentially alter the natural course of the disease.

As used herein, the term "probabilistic map" refers to an anatomical and/or functional map of the brain that determines the spatial/functional consistency of anatomical features and brain activity patterns across a plurality of subjects. The probabilistic maps generate anatomical/functional templates that retain quantitative information on inter-subject variations in brain architecture and functioning. A probabilistic map, incorporating precise statistical information on positional variability of important functional and anatomic interfaces, stores information on the population variability and allows for an identification/representation of the relative number of subjects that include/exhibit a specified feature/functioning. The probabilistic map may indicate a percent value in the range from 0-100 indicating such a relative number.

Referring to FIG. 1, an example of a basic system 10 for identifying/determining an optimal patient-specific neurosurgery target location for a patient of interest in an automated manner is illustrated, in accordance with an embodiment of the invention. The system 10 is depicted as being implemented using a computer 12 that is programmed and/or configured to determine an optimal patient-specific neurosurgery target location (and brain stimulation programming) according to an aspect of the invention. The computer 12 can be a workstation, a standalone computer, a notebook computer, or it can be implemented as part of other microprocessor-based equipment that is programmed based on the teachings contained herein.

The computer 12 includes a processor 14 that is operative to execute instructions for performing the methods described herein. The instructions can be stored in associated memory 16. In the example of FIG. 1, the processor 14 is depicted as running a target locator algorithm 18. Such target locator algorithm 18 can be stored in the memory 16 and loaded into the processor 14 for determining an optimal patient-specific neurosurgery target location for patient treatment, along with (optionally) optimal brain stimulation programming, such as DBS parameters that represent a voltage, frequency, pulse width, and DBS electrode contact used for applying a DBS signal/treatment to achieve an optimal therapeutic effect.

The system 10 can also include a display 20 that can be utilized to represent the results and calculations performed by the target locator algorithm, as well as one or more other input or output devices 22. Such devices 22 can provide an interface through which a user can input data as well as control the target locator algorithm 18. For example, a user can employ the I/O device 22 to input data, such as instructions to initiate or modify the target locator algorithm procedure. The I/O device 22 can also be utilized to interface with an associated treatment device or system, such as a DBS system, to provide an output thereto regarding optimal parameters at which to operate the DBS system, i.e., optimal DBS signals to be applied to a patient for treatment. Still further, the I/O device can be employed to access a brain atlas database, such as from another location in the memory 16 or from another storage location or device, or alternatively processor 14 could access raw data from another location in the memory 16 or from another storage location or device and generate a brain atlas from such data.

Figure 2:
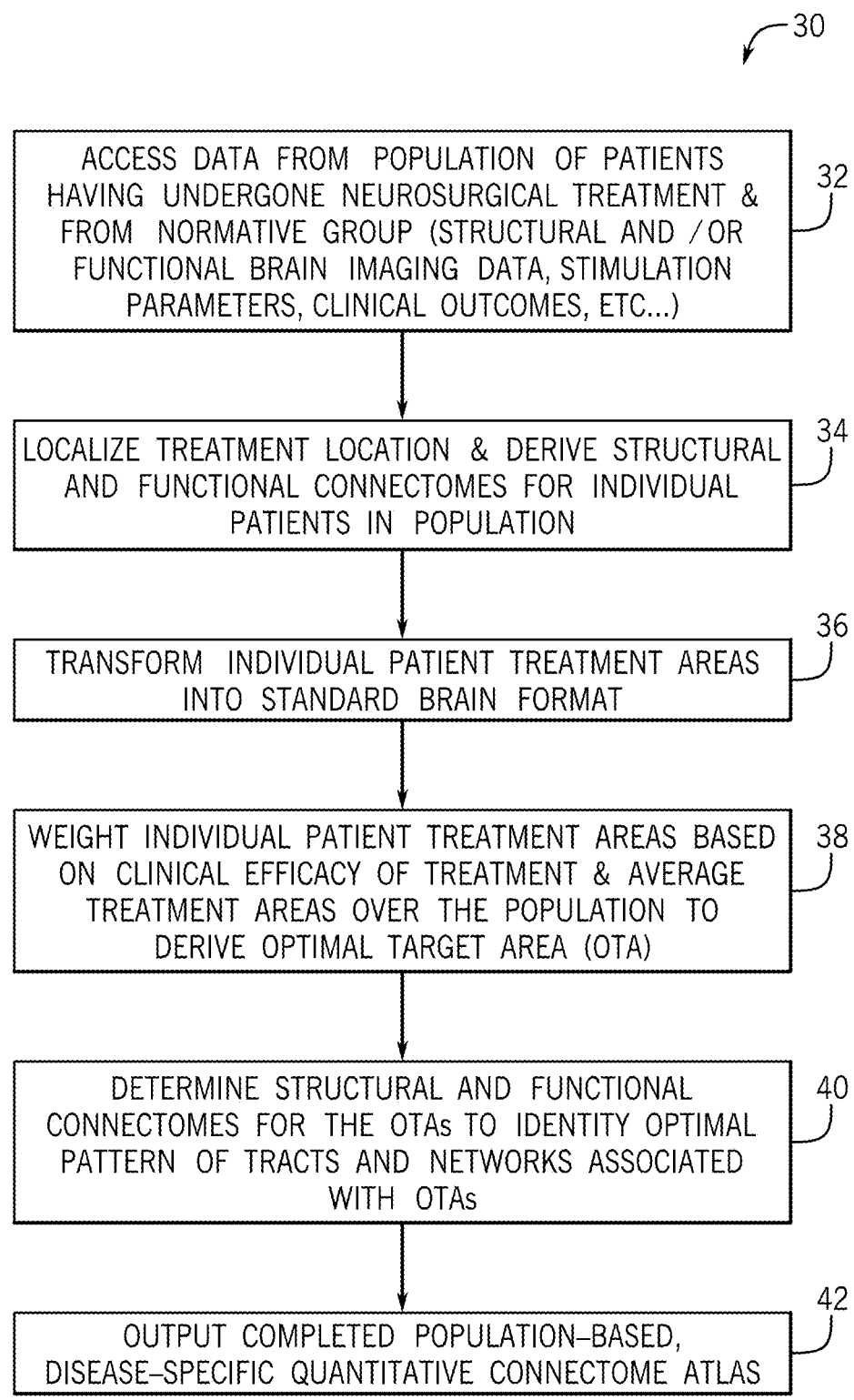
FIG. 2 is a flowchart illustrating a technique for generating a population-based, disease-specific quantitative connectome atlas that identifies target locations, networks, and tracts in the brain associated with optimal stimulation for achieving a best clinical response, according to an embodiment of the invention.

Referring now to FIG. 2, a flowchart is provided illustrating a method 30 for generating a quantitative connectome atlas (i.e., "atlas") that may be used in identifying/determining an optimal patient-specific neurosurgery target location, functional networks, and tracts for a patient of interest in an automated manner. The method 30 may be implemented by a system 10 such as illustrated in FIG. 1, for example, with one or more processors 14 of computer 12 in such a system performing steps and functions described hereafter to generate a quantitative connectome atlas that will be subsequently used in pre-surgical planning to identify a patient-specific neurosurgery target location that will provide maximal symptom relief.

While generation of the atlas is described here below in connection with an atlas that can be used for DBS treatment and optimal patient-specific neurosurgery target location for DBS electrode implantation, it is recognized that the atlas would further include data on other neurosurgery treatments and modality-specific optimal target locations, such as for MR-guided focused ultrasound (MRgFUS), radiosurgery, and radiofrequency ablation, for example.

As shown in FIG. 2, in a first step of method 30 for generating the atlas, data from a large cohort or population of patients having previously undergone modality-specific optimal target locations neurosurgery is accessed at STEP 32, along with a large group of normative/healthy patients. According to an exemplary embodiment, data is provided for hundreds or thousands of patients, so as to provide a significant amount of data from which to generate the atlas. The data from this cohort of patients (and group of normative/healthy patients) can include structural and functional brain imaging data, such as structural magnetic resonance imaging (MM) and functional MM (fMRI) image data for example, as well as a general target location of DBS electrodes implanted in the patients. In one embodiment, functional brain imaging data (e.g., fMRI image data) is acquired from the group of normative/healthy patients.

Data from the cohort of patients accessed at STEP 32 further includes the treatment location (i.e., lesion location for ablative procedure and electrode location for DBS) as well as the stimulation parameters used/applied during treatment, such as, for example, DBS parameters that include voltage, frequency, and pulse width of applied DBS signals, as well as electrode contacts activated to apply the DBS signals. Still further, clinical outcomes for the cohort of patients is also included in the data for each of various disorders. With regard to clinical outcomes recorded/included in the database, such outcomes and/or patient improvement may be provided for patients having a baseline pre-operative and follow-up (>3 months after surgery) clinical scores, and in whom the treatment can be accurately localized, usually implying high spatial resolution neuroimaging data including a baseline pre-operative MRI and immediate post-operative MRI or CT scan. Using appropriate clinical scales for diseases experienced by the patients, the patients' scores were recorded at baseline, and at various time points. For example, the time point with the highest improvement can be chosen and the change in scores calculated—thus providing data on clinical outcomes for the cohort of patients in the database.

In a next step of method 30, localization of the treatment location is performed (i.e., lesion location for ablative procedure and electrode location and corresponding volume of tissue activated (VTA) for DBS) from the patient data, along with a derivation of brain connectivity maps or connectomes from the patient data or normative healthy data, as indicated at STEP 34. With regard to the treatment location localization, such positioning/localization may be achieved via a non-linear normalization of the postoperative MRI images based on the pre-operative MM images—with the treatment location being localized in MNI space using Lead DBS software, for example. Additionally, structural and functional MRI data for each patient or from normative data may be accessed in order to generate structural and functional connectivity maps for each patient that illustrate structurally how different areas of the brain are connected (i.e., a comprehensive map of neural connections in the brain), along with illustrating functioning of the connectome circuits. As an example, in generating the functional connectivity map, an fMRI series may be analyzed to identify couplings between regions of a brain that may work together to perform a particular type of function or to respond to a specific class of stimulus. Such relationships may in some cases be inferred from correlations or covariances among time measurements associated with changes in levels of activation of such regions, such as multiple regions being activated simultaneously responsive to a DBS signal. According to one embodiment, the functional connectome can include psychophysical interaction (PPI) models, ROI resting state models, and voxel-wise resting state models. PPI models can describe connectivity between a ROI (or voxel) and other brain regions, thereby indicating the brain regions where the activity depends on the psychological context and the physiological state of the ROI (or voxel). Resting state models are used to estimate the resting state of a particular ROI, or a region defined by a voxel or set of voxels.

Also at STEP 34, in conjunction with the positioning/localization of the treatment, the structural and functional connectomes may be further analyzed to provide knowledge on general anatomical target locations for treatment and the target connections to other areas/regions of the brain, with the defined zone of ablation (for ablative treatment) or a VTA (that represents the electric field around the electrode where DBS is applied) being derived for such anatomical target locations. For the VTA in the patient, specifics on the stimulation parameters used/applied during DBS treatment (voltage, frequency, pulse width, and active contact) and the electrode location for the electrode are correlated to the VTA, based on information included in or derived from the patient population data. According to an exemplary embodiment, the VTA is estimated based on the DBS settings associated with highest clinical improvement. For example, using Lead DBS software and volume conductor and voltage parameters derived thereby, the potential distribution as a result of the DBS stimulation can be calculated. A derivation of the finite element model can contribute to estimating the VTA using a gradient of potential distribution thresholded at 0.2V/mm, for example.

Upon the derivation of a treatment location for all patients in the patient data group, the method continues at STEP 36 where individual patient treatments are all transformed into a "standard" brain to allow for comparison thereof, with the method 30 then continuing to STEP 38 where individual patient's treatments are weighted by clinical efficacy and/or side-effect minimization. That is, it is recognized that patient improvement and/or side-effect minimization responsive to the neurosurgical treatment may be variable based on a number of factors, including treatment location (relative to the target) and, in the case of DBS, the programming settings used (voltage, frequency, and pulse width). As improvement in a patient's symptoms (and/or minimization of side-effects) are known, along with applied DBS parameters for stimulation procedure, each patient's VTA or ablative lesion may be weighted by clinical efficacy and/or side-effect minimization to account for discrepancy in patient outcome. In an exemplary embodiment, a clinical outcome score may be measured using a recognized scale (e.g., Hamilton Rating Scale for Depression-17 scale for depression subgenual cingulate), with the lesion or VTA then being weighted by the change in clinical score.

Also at STEP 38, the weighted and non-weighted treatment areas (i.e., VTAs or defined zones of ablation) across all patients are averaged over the entire patient population to derive a population-based weighted treatment area (i.e., probabilistic map of efficacy or optimal stimulation) that represents the specific brain area associated with highest clinical improvement and minimal side-effects—also referred to as an optimal target area (OTA) or "seed"—for each disease cohort. According to one embodiment, the probabilistic maps of optimal ablation/stimulation are obtained by different methods, such as by normalizing the product of non-weighted and weighted average maps obtained for each disease or alternatively by average maps masked by frequency or maps made of voxel-wise statistics. Non-weighted average maps were derived from the summation of binarized VTAs/ablation zones at each voxel divided by the total number of patients in the cohort. VTAs/ablation zones were weighted by their corresponding clinical improvement derived from the change between a defined improvement (e.g., the best available score) and the baseline preoperative scores. Weighted average maps were then obtained by calculating the average clinical improvement at the voxel level. Such clinical improvement may reflect general improvement or a specified improvement for a disease, such as a map for tremor, rigidity, or gait improvement in PD, for example.

Upon derivation of the probabilistic maps of efficacy or OTAs for various disease cohorts at STEP 38, the method 30 continues at STEP 40 by determining structural and functional connectivity maps for the probabilistic maps/OTAs using normative data from a healthy control population. That is, using an OTA for each disease cohort, a weighted functional connectome (i.e., population-based weighted connectivity maps) is calculated from normative data and averaged across a large population (e.g., n=1,000 normative subjects). The functional connectome establishes a pattern of tracts and networks associated with the OTA, with these networks and tracts being weighted so as to enable ranking of the networks/tracts. As an example, for a functional connectome for MDD optimal target location (Subgenual Cingulate), the functional connectome could show that for optimal target location DBS, an activation in the orbitofrontal cortex and deactivation in the visual, default-mode and dorsal attention networks should be expected.

In an alternative embodiment, it is recognized that structural and functional connectivity maps for the probabilistic maps/OTAs could be determined by instead averaging structural and functional connectivity maps obtained for each individual treatment area (i.e., VTA or defined zone of ablation).

Thus, according to the steps described above, a completed quantitative functional connectome atlas is generated/output at STEP 42 that enables identification of a convergent "probabilistic zone of optimal stimulation" and their associated connectomes, which are based on treatment localization (i.e., lesion location for ablative procedure and electrode location for DBS), stimulation parameters (for DBS), and clinical outcomes in various disorders. The quantitative functional connectome atlas enables determination of the functional and structural connectivity associated with each probability map of optimal stimulation, in other words identifying an optimal pattern of networks, an optimal network of tracts, and an optimal target location or "anatomical sweet spot". While the optimal pattern of networks and tracts and anatomical sweet spot are in standard space in the atlas, they can be deformed to the brain of a specified patient to provide identification of a patient-specific neurosurgery target location. With individual functional and structural imaging, the normative atlas data can also be used to directly determine in a patient the anatomical area associated with the known optimal pattern of tracts and networks.

Figure 3:
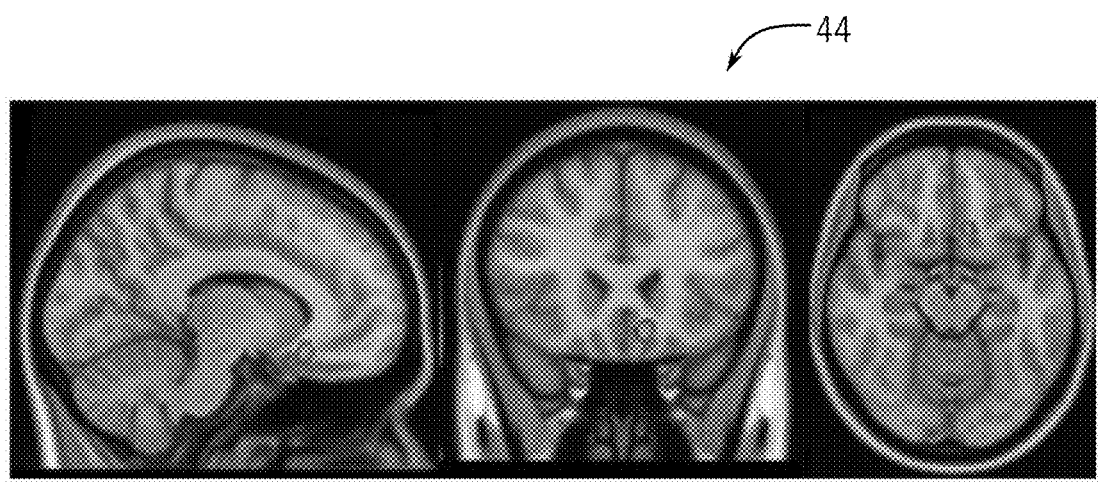
FIG. 3 illustrates a weighted average map showing an OTA, as derived from the method of FIG. 2.
Figure 4:
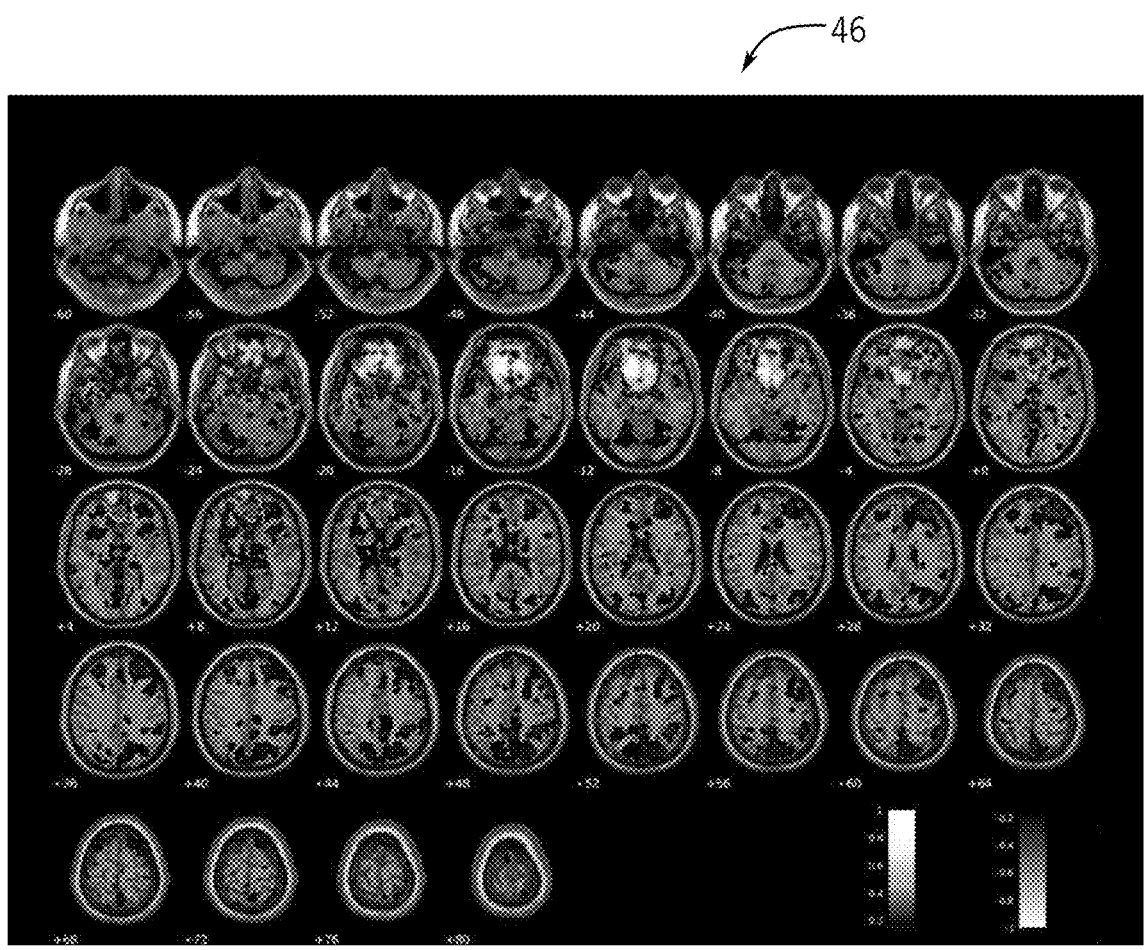
FIG. 4 illustrates an rsfMRI connectivity map of an OTA calculated from normative data and averaged across a large population, as derived from the method of FIG. 2.

FIG. 3 illustrates an example of a weighted average map 44 showing an OTA, as identified/derived at STEP 38 of the method 30. The exemplary weighted average map 44 is a map thresholded at 70% showing an OTA for depression cohort from the population of patients. FIG. 4 illustrates an rsfMRI connectivity map 46 of an OTA calculated from normative data and averaged across a large population, as identified/derived at STEP 40 of the method 30. The rsfMRI connectivity map 46 enables selection/identification of an OTA (and stimulation parameters) for an incoming patient that will produce a connectivity map similar to the rsfMRI connectivity map, as will be explained in greater detail below with respect to the method of FIG. 5.

As set forth above, while the method 30 of FIG. 2 is described in the context with regard to the specific example of DBS treatments and the derivation of a quantitative connectome atlas using determinations/information on electrode localization and VTA determination, it is recognized that the method 30 is not so limited and is applicable to other neurosurgical techniques and diseases. Functional connectomes associated with other functional neurosurgical treatments such as radiosurgery, radiofrequency ablation, and MRgFUS, are also included in the quantitative connectome atlas, and specific measurements/determinations made for such treatments (i.e., ablative lesion localization) may be included in the method 30 as alternatives to the electrode localization and VTA determination. For example, for neurosurgical treatments associated with a lesion, such as MRgFUS and radiosurgery for example, VTA determination can be replaced with manual identification/drawing of lesion(s) in the patient.

Figure 5:
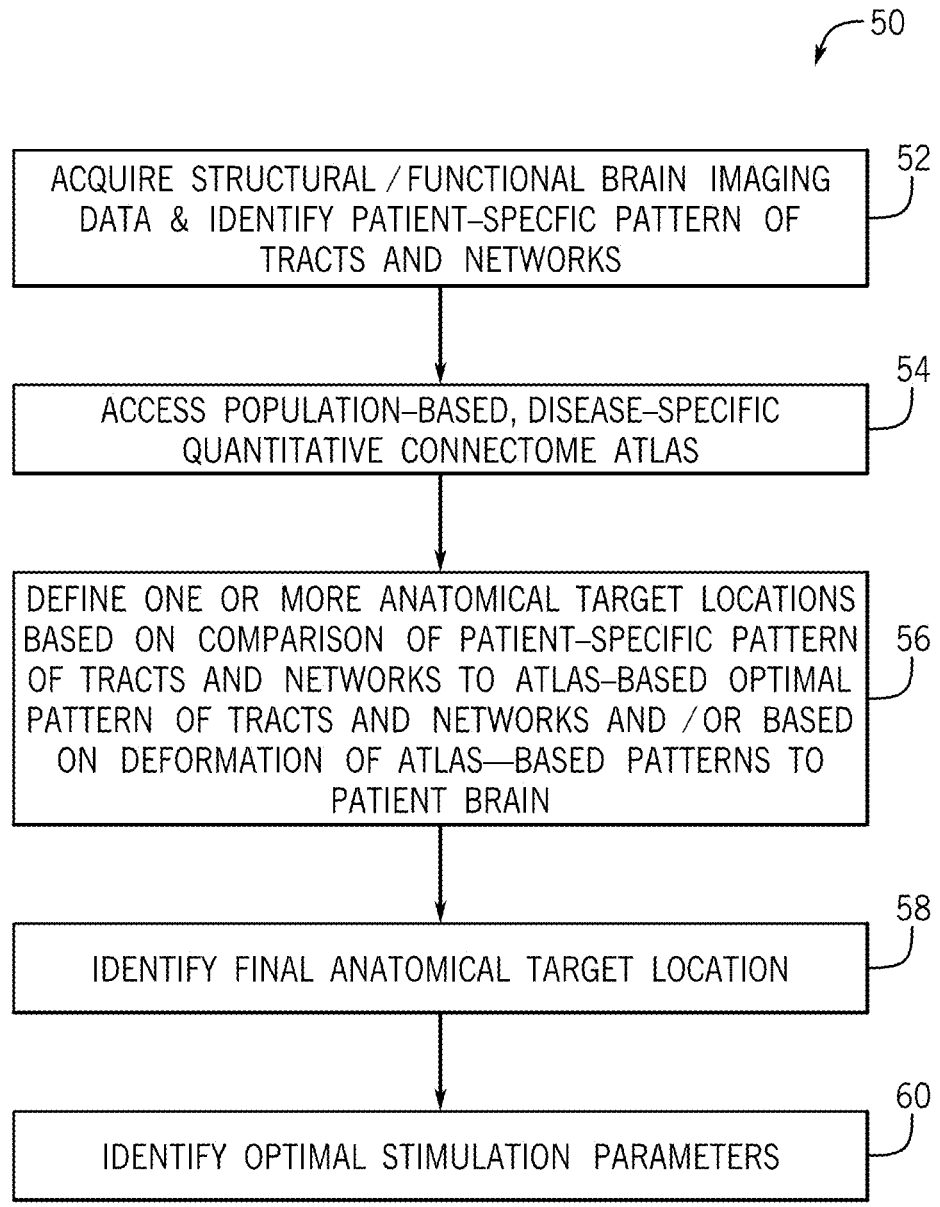
FIG. 5 is a flowchart illustrating a technique for identifying an optimal patient-specific neurosurgery target location for a patient of interest using the quantitative connectome atlas generated in the method of FIG. 2, according to an embodiment of the invention.

Referring now to FIG. 5, a method 50 for personalized functional neurosurgery targeting and brain stimulation programming that can be applied to obtain ideal symptom relief for a patient is illustrated, according to an embodiment of the invention. For a new incoming candidate for neurosurgery, such as a prospective DBS patient, the information included in the atlas (generated by method 30) may be combined with structural and/or functional brain data for the patient in pre-surgical planning to identify a patient-specific neurosurgery target location and brain stimulation programming that will provide maximal symptom relief. The method 50 may be implemented by a system 10 such as illustrated in FIG. 1, for example, with one or more processors 14 of computer 12 in such a system performing steps and functions described hereafter to identify a patient-specific neurosurgery target location and brain stimulation programming that will provide maximal symptom relief.

At STEP 52, one or more of structural and functional MRI data is acquired for the patient. For example, structural MM data may be acquired via a known T1/T2 imaging technique, along with resting-state fMRI (rsfMRI) data that may be acquired via a known fMRI image acquisition process to evaluate regional interactions that occur in the brain in a resting or task-negative state. Such resting brain state conditions are observed through changes in blood flow in the brain which creates what is referred to as a blood-oxygen-level dependent (BOLD) signal that can be measured using fMRI. Additionally, brain imaging data may be acquired via a diffusion-weighted magnetic resonance imaging (DWI or DW-MRI) technique that maps diffusion to provide imaging data on tissue architecture, either normal or in a diseased state, with diffusion tensor imaging (DTI) used to map white matter tractography in the brain being one example. From this structural and functional MRI data, a pattern of tracts and networks can be determined in the patient brain.

According to an exemplary embodiment, and also at STEP 52, upon acquisition of the structural and/or functional image data, preprocessing can be used to standardize image data to known reference images. For example, in several embodiments, rsfMRI data image data can be preprocessed to yield time-series sequence of image data in which brain structures and/or regions within the preprocessed time-series can be identified by the image processing system. According to one embodiment, preprocessing includes realigning and unwarping image data, and despiking image data with respect to movement, variance, and/or any source of noise artifacts as appropriate to the requirements of a given application. In many embodiments, spikes with respect to variance are the result of extreme responses, such as, but not limited to, periods of very high activity followed by periods of very low activity. Preprocessing may further include applying linear co-registration to identified structures in the image data. Realigning and unwarping image data can be used to remove movement artifacts from a fMRI scan time-series of images.

Upon the acquisition of structural and/or functional image data from the patient (and desired preprocessing thereof), a population-based quantitative connectome atlas encompassing various neurological diseases (such as one derived from the method 30 of FIG. 2) is then accessed at STEP 54. Next, one or more anatomical targets in the patient are defined based on the data acquired/processed at STEP 52 and the atlas referenced/accessed at STEP 54, as indicated at STEP 56. That is, according to one embodiment, a comparison between a pattern of the tracts and networks identified from the patient's structural and/or functional MRI data and a pattern of networks and tracts identified in the population-based atlas associated with the OTA (i.e., an optimal pattern of tracts and networks) is performed. The comparison enables identification/selection of the brain region—i.e., seed region or OTA—whose connectivity best matches with the OTA identified in the population-based atlas. This seed region or OTA in the patient is a probabilistic map that, in in combination with the patient-specific structural and/or functional MRI data, allows the surgical team to hone in on the target that overlaps with the optimal anatomical location for treatment. According to another embodiment, rather than using structural and/or functional data from the specific patient, one or more anatomical targets/OTAs in the patient may be defined by deforming/transforming the OTA and associated pattern of tracts and networks from the atlas into standard space to match the patient anatomy (i.e., to match the patient's brain shape).

According to one embodiment, and as shown in FIG. 5, the method 50 may continue at STEP 58, where a final anatomical target location may be determined based on an average of the targets obtained at STEP 56. For example, an average of five targets obtained at STEP 56 may be taken to output/generate a final anatomical target location at STEP 58 at which a functional neurosurgical treatment (e.g., DBS) should be performed for the patient that will provide maximal symptom relief. Also at STEP 58, according to one embodiment, an image/representation of the final anatomical target location that is identified/determined may be displayed (such as on display 20 of FIG. 1) within the patient brain, to provide a visual representation to a clinician of the location. The final anatomical target location may be displayed on a structural or functional image of the patient brain, such as an image derived from a structural or functional MRI scan or a connectome of the patient brain, for example.

Thus, it is seen that—in performing method 50—existing, traditional surgical/clinical tools (e.g., indirect anatomical coordinates, pre-operative T1/T2 imaging, and intra-operative microelectrode recording for neurosurgeons, empiric algorithms for programming clinicians) may be used in conjunction with the population-based quantitative connectome atlas (derived in FIG. 2) to provide patient-specific neurosurgery target location.

While the description of method 50 set forth above is with regard to identifying a patient-specific neurosurgery target location, it is recognized that use of the population-based quantitative connectome atlas also provides for identification of optimal stimulation parameters that may be applied at the target location. That is, as the population-based quantitative connectome atlas includes not only population-based data on ideal neurosurgery target locations for each of various disorders, but also data on (1) the stimulation parameters used/applied during treatment, such as DBS parameters including voltage, frequency, and pulse width of applied DBS signals, as well as electrode contacts activated to apply the DBS signals, for example, and (2) clinical outcomes for the cohort of patients achieved using those stimulation parameters, optimal stimulation parameters may be estimated for the patient. Thus, optionally at STEP 60, an optimal set of stimulation parameters used for patient treatment may be identified that enables post-surgical fine-tuning of neuromodulation and should provide maximal symptom relief and minimal adverse effects. In identifying these parameters, the identification of the brain region (seed region or OTA) whose connectivity best matches with the OTA identified in the population-based atlas may be followed by identification of stimulation parameters associated with the OTA identified in the population-based atlas (i.e., what stimulation parameters were used to generate the VTAs/OTA identified in the population-based atlas to elicit an optimal patient response).

Figure 6:
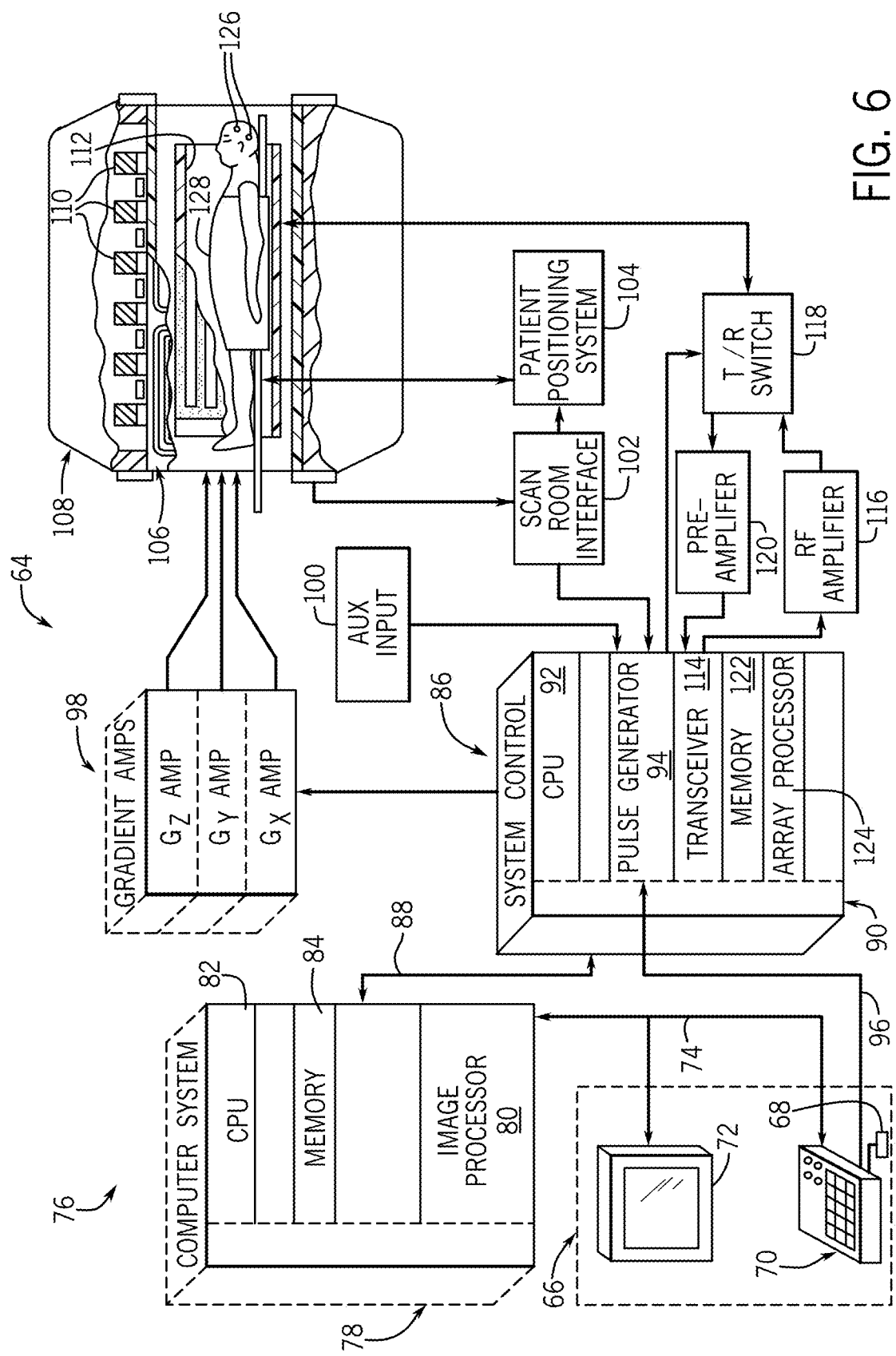
FIG. 6 is a schematic diagram of an exemplary MRI system usable with the method of FIG. 4, according to an embodiment of the invention.
Figure 7:
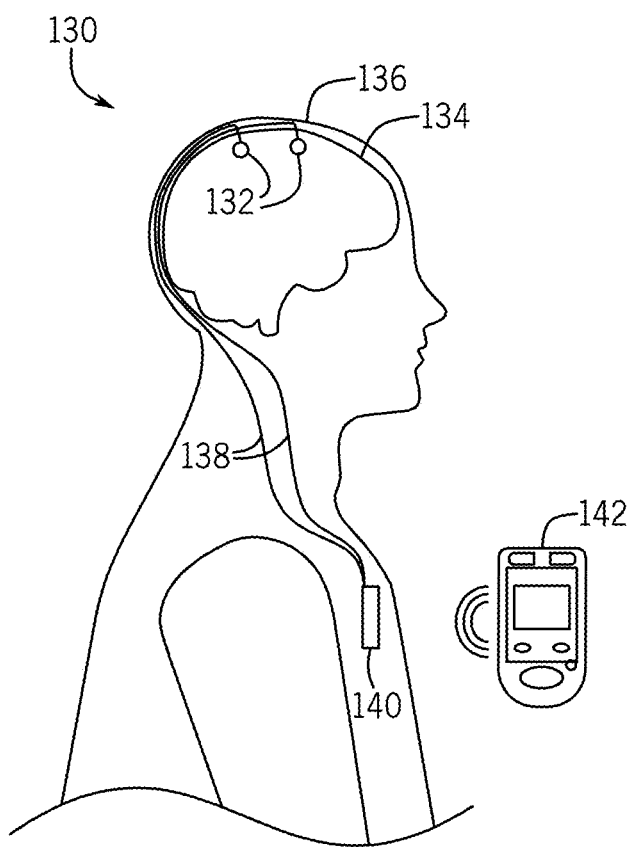
FIG. 7 is a schematic diagram a deep brain stimulation (DBS) treatment system usable with the method of FIG. 4, according to an embodiment of the invention.

Referring now to FIGS. 6 and 7, imaging and treatment systems that may be used in connection with method 50 are illustrated according to an embodiment of the invention—with such systems being used to acquire patient-specific structural and functional brain imaging data (STEP 52) and to provide treatment to the patient upon completion of method 50, such as by applying an optimal set of stimulation parameters (STEP 60). While an MRI system and DBS system are shown in FIGS. 6 and 7, respectively, it is recognized that other imaging and treatment systems may be used in association with the method, and thus embodiments of the invention are not meant to be limited only to the systems shown in FIGS. 6 and 7.

Referring first to FIG. 6, an exemplary MRI system 64 useable with the method 50 is illustrated, with the major components of the MRI system 64 being shown therein. The operation of the Mill system 64 is controlled for certain functions from an operator console 66, which in this example includes a keyboard or other input device 68, a control panel 70, and a display screen 72. The input device 68 can include a mouse, joystick, keyboard, track ball, touch activated screen, light wand, voice control, card reader, push-button, or any similar or equivalent input device, and may be used for interactive geometry prescription. The operator console 66 communicates through a link 74 with a separate computer system 76 that enables an operator to control the production and display of images on the display screen 72. The computer system 76 includes a number of modules which communicate with each other through a backplane 78. These modules include an image processor module 80, a CPU module 82 and a memory module 84, known in the art as a frame buffer for storing image data arrays. The computer system 76 communicates with a separate system control 86 through a high-speed serial link 88.

The system control 86 includes a set of modules connected together by a backplane 90. These include a CPU module 92 and a pulse generator module 94 which connects to the operator console 66 through a serial link 96. It is through serial link 96 that the system control 86 receives commands from the operator to indicate the scan sequence that is to be performed. The pulse generator module 94 operates the system components to carry out the desired scan sequence and produces data which indicates the timing, strength and shape of the radio frequency (RF) pulses produced, and the timing and length of the data acquisition window. The pulse generator module 94 connects to a set of gradient amplifiers 98, to indicate the timing and shape of the gradient pulses that are produced during the scan. The pulse generator module 94 can also receive timing data through an auxiliary trigger input 100. And finally, the pulse generator module 94 connects to a scan room interface circuit 102 which receives signals from various sensors associated with the condition of the patient and the magnet system. It is also through the scan room interface circuit 102 that a patient positioning system 104 receives commands to move the patient to the desired position for the scan.

The gradient waveforms produced by the pulse generator module 94 are applied to the gradient amplifier system 98 having Gx, Gy, and Gz amplifiers. Each gradient amplifier excites a corresponding physical gradient coil in a gradient coil assembly generally designated 106 to produce the magnetic field gradients used for spatially encoding acquired signals. The gradient coil assembly 106 forms part of a resonance assembly 108 which includes a polarizing magnet 110 and a whole-body RF coil 112. A transceiver module 114 in the system control 86 produces pulses which are amplified by an RF amplifier 116 and coupled to the whole-body RF coil 112 by a transmit/receive switch 118. The resulting signals emitted by the excited nuclei in the patient may be sensed by the same whole-body RF coil 112 and coupled through the transmit/receive switch 118 to a preamplifier 120. The amplified MR signals are demodulated, filtered, and digitized in the receiver section of the transceiver module 114. The transmit/receive switch 118 is controlled by a signal from the pulse generator module 94 to electrically connect the RF amplifier 116 to the whole-body RF coil 112 during the transmit mode and to connect the preamplifier 120 to the whole-body RF coil 112 during the receive mode. The transmit/receive switch 118 can also enable a separate RF coil (for example, a surface coil) to be used in either the transmit or receive mode.

The MR signals picked up by the whole-body RF coil 112 are digitized by the transceiver module 114 and transferred to a memory module 122 in the system control 86. A scan is complete when an array of raw k-space data has been acquired in the memory module 122. This raw k-space data is rearranged into separate k-space data arrays for each image to be reconstructed, and each of these is input to an array processor 124 which operates to Fourier transform the data into an array of image data. This image data is conveyed through the serial link 88 to the computer system 76 where it is stored in memory. In response to commands received from the operator console 66 or as otherwise directed by the system software, this image data may be archived in long term storage or it may be further processed by the image processor module 80 and conveyed to the operator console 66 and presented on the display screen 72.

According to some embodiments of the invention, MRI system 64 is operated to enable optimized visualization and localization of DBS electrodes 1326 post-operatively within a patient 128 to provide for localization thereof, with acquisition of the image data and subsequent analysis and processing of the image data by computer system 76 being selectively controlled to achieve such optimization.

Referring now to FIG. 7, a deep brain stimulation (DBS) treatment system 130 is illustrated that may be employed to apply optimal stimulation parameters as determined at STEP 60 of method 50 (FIG. 5). The DBS system 130 includes one or more leads or electrodes 132 surgically implanted within one or more regions of the brain 134 of a patient 136. Each implanted electrode 132 is configured to apply stimulation signals to a targeted region of the brain 134. While two electrodes 132 are illustrated, it will be understood that system 130 may include a single implanted electrode as well as three or more electrodes, each of which may be positioned and configured to facilitate unipolar or bipolar stimulation.

Each implanted electrode 132 is connected through an extension wire 138 that is passed under the skin of the patient 136 to a pulse generator 140 configured to deliver stimulation signals to electrodes 132. Pulse generator 140 may include a power supply (not shown) such as a battery or other type of power storage device and microelectronic circuitry (not shown) that may include hardware and/or software for generating and outputting stimulation signals in response to control signals or commands. In some embodiments, pulse generator 140 may further include a storage unit (not shown) that permits patient-specific data to be stored within the pulse generator 140.

In the illustrated embodiment, pulse generator 140 is an internal pulse generator that is implanted beneath the skin of the patient 136, such as, for example, under the clavicle as shown in FIG. 7. However, internal pulse generator 140 may be located elsewhere within the patient 136 in alternative embodiments such as, for example, lower in the chest or over the abdomen. In alternative embodiments, pulse generator 140 may be an external device coupled to implanted electrodes 132.

Figure 8:
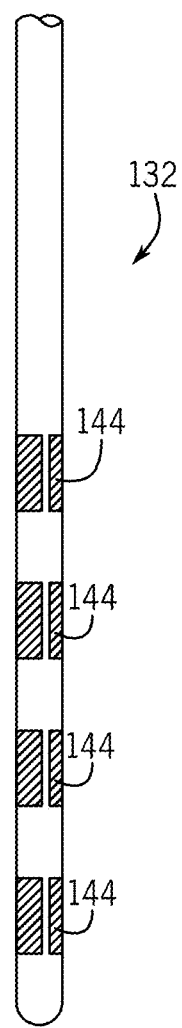
FIG. 8 is a schematic diagram of an exemplary DBS electrode used in the DBS system of FIG. 5.

In the case of an implanted pulse generator, the pulse generator 140 is programmed with a wireless device 142 that is held over the skin of the patient 136 proximate the implanted location of the pulse generator 140. The programming defines the excitation parameters of the DBS, which can be adjusted as the patient's condition changes over time. The circuitry within the pulse generator 140 generates pulse sequences in accordance with the stimulation parameters that send excitation signals to implanted electrodes 132. The stimulation can be provided in a cycling fashion and at various voltages, frequencies, and pulse widths, based on the desired treatment. Additionally, different contacts 144 of the electrodes 132 may be selectively activated to apply the stimulation, as illustrated in FIG. 8. According to an embodiment of the invention, the pulse generator 140 may be programmed (either directly or via wireless device 142) to generate pulse sequences comprising the optimal stimulation parameters as determined at STEP 60 of method 50, with the DBS signals/sequences including voltages, frequencies, pulse widths, and contact location, determined to provide maximal symptom relief to the patient.

Beneficially, embodiments of the invention thus provide a system and method for personalized functional neurosurgery targeting and brain stimulation programming. Accurate neurosurgery targeting is achieved via use of a population-based brain connectivity atlas encompassing various neurological diseases, with the atlas being used in pre-surgical planning to identify a patient-specific neurosurgery target location that will provide maximal symptom relief. The atlas enables identification of a convergent "probabilistic zone of optimal stimulation" and their associated connectomes, which are based on DBS lead/electrode localization, stimulation parameters, and clinical outcomes in various disorders. The atlas enables determination of the functional and structural connectivity associated with each probability map of optimal stimulation, along with identifying an optimal pattern of networks, an optimal network of tracts, and an optimal target location or "anatomical sweet spot" from the structural and functional connectivity maps. The atlas also provides for determination of an optimal set of stimulation parameters used for patient treatment, so as to enable post-surgical fine-tuning of neuromodulation that will provide maximal symptom relief.

A technical contribution for the disclosed method and apparatus is that it provides for a computer implemented system and method for personalized functional neurosurgery targeting and brain stimulation programming.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to one embodiment of the invention, a system for identifying a patient-specific neurosurgery target location is provided. The system includes a processor programmed to receive brain imaging data for a patient that includes tracts and networks in the patient brain, access a quantitative connectome atlas comprising population-based, disease-specific structural and functional connectivity maps comprising a pattern of tracts and networks associated with an optimal target area (OTA) identified from a population of patients, and define the patient-specific neurosurgery target location based on a comparison between a pattern of the tracts and networks from the brain imaging data for the patient and the pattern of tracts and networks associated with the OTA identified from the population of patients in the quantitative connectome atlas.

According to another embodiment of the invention, The method includes accessing a database comprising data on a population of patients having previously undergone functional neurosurgical treatment and on a healthy control population of patients, the data comprising structural and/or functional brain imaging data, and clinical outcomes for the population of patients, for each of a plurality of diseases. The method also includes identifying a treatment area for each patient in the population, the treatment area comprising a lesion location when the functional neurosurgical treatment is an ablative procedure or an electrode location, and corresponding volume of tissue activated (VTA) when the functional neurosurgical treatment is deep brain stimulation (DBS). The method further includes weighting the treatment area for each patient based on symptom improvement resulting from the functional neurosurgical treatment and averaging the weighted treatment areas across the population of patients to identify an optimal target area (OTA) associated with a maximal clinical improvement in each of a number of disease cohorts in the population of patients.

According to yet another embodiment of the invention, a computer-based method for identifying a patient-specific neurosurgery target location is provided. The method includes accessing a population-based, disease-specific brain connectivity atlas derived from a population of patients having previously undergone functional neurosurgical treatment, with data collected on each of the patients comprising brain imaging data and clinical outcomes for the patient, for each of a plurality of diseases. The method also includes identifying, from the brain connectivity atlas, one or more optimal neurosurgery target locations associated with optimal treatment of the patient.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for identifying a patient-specific neurosurgery target location, the system comprising:
    a processor programmed to:
        receive brain imaging data for a patient that includes tracts and networks in the patient brain;
        access a quantitative connectome atlas comprising population-based, disease-specific structural and functional connectivity maps comprising a pattern of tracts and networks associated with an optimal target area (OTA) identified from a population of patients; and
        define the patient-specific neurosurgery target location based on a comparison between a pattern of the tracts and networks from the brain imaging data for the patient and the pattern of tracts and networks associated with the OTA identified from the population of patients in the quantitative connectome atlas.

2. The system of claim 1, wherein in defining the patient-specific neurosurgery target location, the processor is programmed to match the pattern of tracts and networks in the patient brain imaging data to the pattern of tracts and networks associated with the OTA identified from the population of patients in the quantitative connectome atlas, and to generate a probabilistic map.

3. The system of claim 2, wherein the processer is further programmed to select the best match from the probabilistic map to identify the patient-specific neurosurgery target location.

4. The system of claim 3, wherein the processor is further programmed to determine an optimal set of deep brain stimulation (DBS) parameters to be used for patient treatment at the patient-specific neurosurgery target location.

5. The system of claim 4, wherein in determining the optimal set of DBS parameters, the processor is programmed to identify an optimal combination of signal voltage, signal frequency, signal pulse-width, and an activated electrode contact.

6. The system of claim 1, wherein the quantitative connectome atlas comprises data on a population of patients having previously undergone functional neurosurgical treatment and data on a healthy control population, the data comprising patient brain imaging data, parameters of a stimulation used during the functional neurosurgical treatment, and clinical outcomes for the population of patients, for each of a plurality of diseases.

7. The system of claim 6, wherein the functional neurosurgical treatment comprises a lesioning procedure or stimulation procedure, and wherein the quantitative connectome atlas further comprises data on a location of an ablative treatment or a location of one or more electrodes implanted in the patient for stimulation.

8. The system of claim 7 wherein, the processor is further programmed to generate the quantitative connectome atlas by:
    identifying, for each patient in the population, a treatment area derived from the brain imaging data, the treatment area comprising a lesion location or electrode location and corresponding volume of tissue activated (VTA);
    weighting the treatment area for each patient based on one or more of symptom improvement and side-effect minimization resulting from the functional neurosurgical treatment; and
    averaging the weighted treatment area across the population of patients to identify the OTA; and
    determining structural and functional connectivity maps for the OTA using data from the population of patients and the healthy control population.

9. The system of claim 8, wherein generation of quantitative connectome atlas further comprises averaging structural and functional connectivity maps obtained for the treatment area of each patient in the population.

10. The system of claim 1, wherein the brain imaging data comprises magnetic resonance imaging (MRI) data.

11. The system of claim 1, wherein the neurosurgery target location in the patient is disease-specific and functional neurosurgery technique-specific, with the pattern of tracts and networks associated with an OTA differing between diseases and functional neurosurgery techniques.

12. A computer-based method for deriving a disease-specific, population-based quantitative connectome atlas, the method comprising:
    accessing a database comprising data on a population of patients having previously undergone functional neurosurgical treatment and on a healthy control population of patients, the data comprising structural and/or functional brain imaging data, and clinical outcomes for the population of patients, for each of a plurality of diseases;
    identifying a treatment area for each patient in the population, the treatment area comprising a lesion location when the functional neurosurgical treatment is an ablative procedure or an electrode location, and corresponding volume of tissue activated (VTA) when the functional neurosurgical treatment is deep brain stimulation (DBS);
    weighting the treatment area for each patient based on symptom improvement resulting from the functional neurosurgical treatment; and
    averaging the weighted treatment areas across the population of patients to identify an optimal target area (OTA) associated with a maximal clinical improvement in each of a number of disease cohorts in the population of patients.

13. The computer-based method of claim 12 further comprising performing a step of localizing the treatment area.

14. The computer-based method of claim 12 further comprising determining structural and functional connectivity maps for the OTAs using disease-specific functional brain imaging data or data from the healthy control population of patients, the connectivity maps establishing a pattern of optimal tracts and networks associated with the OTAs.

15. The computer-based method of claim 12 wherein, in identifying the OTA for a disease cohort, the method further comprises:
    averaging non-weighted treatment areas across the population of patients; and identifying the OTA for the disease cohort via one of normalizing a product of the weighted and non-weighted treatment areas, using average maps masked by frequency, or using maps made of voxel-wise statistics.

16. A computer-based method for identifying a patient-specific neurosurgery target location, the method comprising:
    accessing a population-based, disease-specific brain connectivity atlas derived from a population of patients having previously undergone functional neurosurgical treatment, with data collected on each of the patients comprising brain imaging data and clinical outcomes for the patient, for each of a plurality of diseases; and
    identifying from the brain connectivity atlas, one or more optimal neurosurgery target locations associated with optimal treatment of the patient; and
    further comprising:
        receiving brain imaging data for the patient comprising tracts and networks in the patient brain;
        comparing the tracts and networks in the patient brain to an optimal target area (OTA) derived from the brain connectivity atlas and to an optimal pattern of tracts and networks associated with the OTA; and
        identifying a patient OTA that best matches with the OTA from the brain connectivity atlas to identify the one or more optimal neurosurgery target locations.

17. The computer-based method of claim 16, wherein the brain imaging data for the patient comprises magnetic resonance imaging (MRI) data.

18. A computer-based method for identifying a patient-specific neurosurgery target location, the method comprising:
    accessing a population-based, disease-specific brain connectivity atlas derived from a population of patients having previously undergone functional neurosurgical treatment, with data collected on each of the patients comprising brain imaging data and clinical outcomes for the patient, for each of a plurality of diseases; and
    identifying from the brain connectivity atlas, one or more optimal neurosurgery target locations associated with optimal treatment of the patient; and
    further comprising:
        identifying an optimal target area (OTA) from the brain connectivity atlas and an optimal pattern of tracts and networks associated therewith; and
        deforming the OTA and associated optimal pattern of tracts and networks to the brain of the patient to identify the one or more optimal neurosurgery target locations.

19. The computer-based method of claim 18 further comprising determining an optimal set of DBS parameters to be used for patient treatment at the neurosurgery target location that achieves the optimal treatment of the patient.

20. A computer-based method for identifying a patient-specific neurosurgery target location, the method comprising:
    accessing a population-based, disease-specific brain connectivity atlas derived from a population of patients having previously undergone functional neurosurgical treatment, with data collected on each of the patients comprising brain imaging data and clinical outcomes for the patient, for each of a plurality of diseases; and
    identifying from the brain connectivity atlas, one or more optimal neurosurgery target locations associated with optimal treatment of the patient;
    wherein the functional neurosurgery to be performed on the patient comprises deep brain stimulation (DBS) treatment, and wherein the quantitative connectome atlas comprises data on a location of one or more DBS electrodes implanted in the patient and parameters of a DBS used during the functional DBS treatment.

* * * * *